US009889088B2

(12) United States Patent
Dibas et al.

(10) Patent No.: US 9,889,088 B2
(45) Date of Patent: Feb. 13, 2018

(54) ALPHA-2 ADRENERGIC AGONIST HAVING LONG DURATION OF INTRAOCULAR PRESSURE-LOWERING EFFECT

(75) Inventors: Mohammed I. Dibas, Mission Viejo, CA (US); Daniel W. Gil, Corona Del Mar, CA (US); John E. Donello, Dana Point, CA (US)

(73) Assignee: Allergan, Inc., Irvine, CA (US)

( * ) Notice: Subject to any disclaimer, the term of this patent is extended or adjusted under 35 U.S.C. 154(b) by 264 days.

(21) Appl. No.: 13/010,958

(22) Filed: Jan. 21, 2011

(65) Prior Publication Data
US 2011/0178145 A1      Jul. 21, 2011

Related U.S. Application Data

(60) Provisional application No. 61/296,912, filed on Jan. 21, 2010.

(51) Int. Cl.
*A61K 31/4184* (2006.01)
*A61K 9/00* (2006.01)

(52) U.S. Cl.
CPC ........ *A61K 9/0048* (2013.01); *A61K 31/4184* (2013.01)

(58) Field of Classification Search
CPC ................................................ A61K 31/4184
See application file for complete search history.

(56) References Cited

U.S. PATENT DOCUMENTS

| 6,316,637 B1* | 11/2001 | Jeon et al. | 548/306.1 |
| 6,495,583 B1 | 12/2002 | Jeon et al. | |
| 2005/0244463 A1 | 11/2005 | Huang et al. | |
| 2010/0015158 A1* | 1/2010 | Robinson et al. | 424/141.1 |

FOREIGN PATENT DOCUMENTS

| WO | 95-16685 | 6/1995 |
| WO | 96-04270 | 2/1996 |
| WO | 2005-110368 A1 | 11/2005 |
| WO | 2005110368 A1 | 11/2005 |
| WO | 2007005177 A1 | 1/2007 |
| WO | 2007090793 A1 | 8/2007 |

OTHER PUBLICATIONS

Anna Galanopoulos, 2009, Clinical Efficacy and neuroprotective Effects of Brimonidine in the Management of Glaucoma and Ocular Hypertension, Clinical Ophthalmology, 3, 117-122.
H.N. Shivakumar, Nov. 2007, Design of Ocular Inserts of Brimonidine Tartrate by Response Surface Methodology, Journal of Drug Delivery Science and Technology, 17(6), 421-430.
J. Ni, "Characterization of benzimidazole and other oxidative and conjugative metabolites of brimonidine in vitro and in rats in vivo using on-line H/D exchange LC-MS/MS and stable-isotope tracer techniques", Xenobiotica, Feb. 2007; 37(2): 205-220.
Robert Noecker, "Ophthalmic Preservatives: Considerations for Long-term Use in Patients With Dry Eye or Glaucoma", Review of Ophthalmology, Continuing Medical Education—Jun. 2001.
Chapter 14 Preparations for Dry Eye and Ocular Surface Disease, pp. 266-272.
P. Heinrich Stahl. "Handbook of Pharmaceutical Salts Properties, Selection. and Use", International Union of Pure and Applied Chemistry (IUPAC) 2002, pp. 329-345.
Andrew A. Acheampong, "Comparative Ocular Pharmacokinetics of Brimonidine After a Single Dose Application to the Eyes of Albino and Pigmented Rabbits", Department of Pharmacokinetics, Allergan Pharmaceuticals, vol. 23. No. 7, Aug. 5, 1994, pp. 708-712.
Du-Shieng Chien, "Corneal and Conjunctival/Scleral Penetration of P-Aminoclonidine, AGN 190342, and Clonidine in Rabbit Eyes", Departments of Pharmacokinetics and 'Chemical Sciences, Allergan Pharmaceuticals, vol. 9, 1990.

* cited by examiner

*Primary Examiner* — Zohreh Fay
(74) *Attorney, Agent, or Firm* — Barbara C. Potts

(57) ABSTRACT

The present invention provides a method of lowering intraocular pressure which comprises administering a therapeutically effective amount of a pharmaceutical composition comprising 4-bromo-5-(2-imidazolin-2-ylamino)benzimidazole, or a salt thereof to the affected eye of a patient, as a single dose, wherein the affected eye has an intraocular pressure less than the baseline intraocular pressure for at least eight (8) hours.

13 Claims, 4 Drawing Sheets

ALPHA-2 ADRENERGIC AGONIST HAVING LONG DURATION OF INTRAOCULAR PRESSURE-LOWERING EFFECT

RELATED APPLICATION

This application claims the benefit of U.S. Provisional Application Ser. No. 61/296,912, filed Jan. 21, 2010, the disclosure of which is hereby incorporated in its entirety herein by reference.

BACKGROUND OF THE INVENTION

The present invention relates to a method of lowering intraocular pressure of a patient in need thereof which comprises administering a therapeutically effective amount of a composition comprising an alpha-2 adrenergic receptor agonist to the affected eye of said patient wherein the intraocular-lowering effect on the treated eye remains less than the baseline intraocular pressure for at least eight (8) hours.

SUMMARY OF THE RELATED ART

Alpha-2 adrenergic receptor agonists play a key role in modulating aqueous humor formation and facilitating aqueous outflow; as a result these compounds lower intraocular pressure in glaucomatous patients. Glaucoma is a condition that can cause damage to the optic nerve and vision loss, usually due to increased pressure in the eye. There are only two alpha-2 adrenergic drugs prescribed for lowering intraocular pressure. The compound (5-bromo-quinoxalin-6-yl)-imidazolidin-2-ylidene-amine, generically known as, brimonidine tartrate, sold under the trademark ALPHAGAN® P (available from Allergan, Inc.) is currently prescribed for long-term treatment of glaucomatous patients. While brimonidine tartrate is effective at lowering elevated intraocular pressure, it is approved only for a 3 times per day dosing regimen, effectively managing intraocular pressure in glaucomatous patients. Considering the aged glaucomatous patient population, a 3 times per day dosing frequency is far from optimal and may result in poor patient compliance.

The other alpha-2 adrenergic drug is the compound 2,6-dichloro-N-imidazolidin-2-ylidene-benzene-1,4-diamine, generically known as, apraclonidine hydrochloride sold under the trademark IOPIDINE® (available from Alcon Pharmaceuticals). Apraclonidine hydrochloride is only approved for the short-term to control or prevent postsurgical elevations in intraocular pressure that occur in patients after argon laser trabeculoplasty, argon laser iridotomy or Nd:YAG posterior capsulotomy. Apraclonidine hydrochloride is known to cause side effects such as severe allergic reactions.

Brimonidine and apraclonidine are two compounds within the 2-imidazolidinyleneamino alpha-2 agonist structural class.

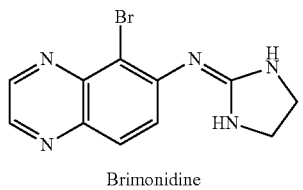
Brimonidine

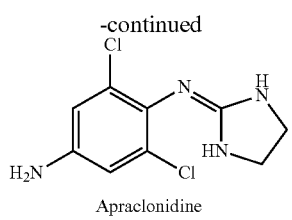
Apraclonidine

As described, these compounds transiently lower intraocular pressure. Previous pharmacokinetics studies (Published data in Acheampong et al. (*Drug Metabolism and Disposition,* 1995 Vol 23, No. 7, p 708-712 and Chein et al. (*Curr. Eye Res.* 1990 9(11):1051-9) demonstrated that brimonidine and apraclonidine readily pass through the cornea and sclera following topical dosing, and are rapidly cleared from the aqueous humor.

BRIEF SUMMARY OF THE INVENTION

We have now discovered that compound, 4-bromo-N-imidazolidin-2-ylidene-1-H-benzimidazol-5-amine, unexpectedly lowers intraocular pressure for a prolonged period and adequately manages intraocular pressure, with dosing less than 3 times per day, e.g. once or twice per day. The compound 4-bromo-N-imidazolidin-2-ylidene-1-H-benzimidazol-5-amine, also a 2-imidazolidinyleneamino derivative, surprisingly has a long duration of action that could not be anticipated by the literature or its structure.

The structure of 4-bromo-N-imidazolidin-2-ylidene-1-H-benzimidazol-5-amine is as follows:

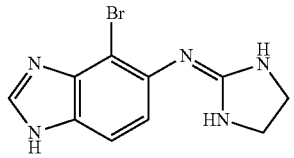 [SMILES: Brc1c(N=C2NCCN2)ccc2[nH]cnc12]

Compound 4-bromo-N-imidazolidin-2-ylidene-1-H-benzimidazol-5-amine may be prepared according to the disclosure of U.S. Pat. No. 6,495,583 B1 which is hereby incorporated by reference in its entirety. Acheampong et al. have shown in *Xenobiotica,* February 2007, Vol. 37(2), pages 205-220 that this compound was found in trace amounts in the urine of rats after administration of an oral dose of brimonidine tartrate.

When administered topically in normotensive rabbits, this compound lowers intraocular pressure with unexpected long duration of action, i.e. up to 8 hours or more, with no systemic side effects when compared to other alpha-2 agonists. Drugs in this class may cause fatigue and/or drowsiness in some patients. In addition, this compound shows unexpectedly long intraocular pressure lowering, when administered topically to hypertensive monkeys.

Surprisingly, despite the high structural similarity to brimonidine and apraclonidine, the 2-imidazolidinyleneamino alpha-2 agonist of the present invention has sustained level of drug being maintained for a long period of time unlike brimonidine. Nevertheless, pharmacokinetic analysis demonstrate that the level of the 2-imidazolidinyleneamino alpha-2 agonist of the present invention, in the aqueous humor is readily maintained for a prolonged period of time, at least eight (8) hours after single dose administration, unlike brimonidine. Published data by Acheampong et al.

(*Drug Metabolism and Disposition*, Vol 23, No. 7, p 708-712) show that increasing the amount of brimonidine does not improve its half life in the aqueous humor and results in increased systemic exposure unlike the compound of the present invention. Pharmacokinetic analysis also showed that the alpha-2 agonist of the present invention has undetectable levels in the systemic circulation indicating that said 2-imidazolidinyleneamino alpha-2 agonist poses less systemic side effects.

It has been found that brimonidine and apraclonidine accumulate in the iris-ciliary body due to their high binding to the pigment melanin. On the contrary, unpublished pharmacokinetic data showed that the 2-imidazolidinyleneamino alpha-2 agonist of the present invention shows very little accumulation at the iris-ciliary body and no sign of melanin binding. Thus, said compound 4-bromo-N-imidazolidin-2-ylidene-1-H-benzimidazol-5-amine has unique and unexpected properties that enable its utilization for elevated intraocular pressure in glaucomatous patients. The use of compound 4-bromo-N-imidazolidin-2-ylidene-1-H-benzimidazol-5-amine shows huge benefits such as extended duration and long term managing without side effects unlike brimonidine and apraclonidine.

This invention provides a method for lowering intraocular pressure in glaucoma by the administration of 4-bromo-N-imidazolidin-2-ylidene-1-H-benzimidazol-5-amine or a pharmaceutically-acceptable salt thereof.

The term "pharmaceutically acceptable salts" according to the invention include therapeutically active, non-toxic base or acid salt forms, which compound 4-bromo-N-imidazolidin-2-ylidene-1-H-benzimidazol-5-amine is able to form.

The acid addition salt form of 4-bromo-N-imidazolidin-2-ylidene-1-H-benzimidazol-5-amine that occurs in its free form as a base, can be obtained by treating the free base with an appropriate acid such as an inorganic acid, for example hydrochloric acid, hydrobromic acid, sulfuric acid, phosphoric acid, nitric acid and the like; or an organic acid such as for example, acetic, hydroxyacetic, propanoic, lactic, pyruvic, malonic, fumaric acid, maleic acid, oxalic acid, tartaric acid, succinic acid, malic acid, ascorbic acid, benzoic acid, tannic acid, pamoic acid, citric, methylsulfonic, ethanesulfonic, benzenesulfonic, formic and the like (Handbook of Pharmaceutical Salts, P. Heinrich Stahal & Camille G. Wermuth (Eds), Verlag Helvetica Chimica Acta-Zürich, 2002, 329-345).

4-bromo-N-imidazolidin-2-ylidene-1-H-benzimidazol-5-amine and its pharmaceutically-acceptable salts have extended alpha-2 adrenergic receptor agonist activity in lowering intraocular pressure and may be administered through different routes, including but not limited to topical eye drops, direct injection, application at the back of the eye or formulations that may further enhance the long duration of actions such as a slow releasing pellet, suspension, gel, or sustained delivery devices such as any suitable drug delivery system (DDS) known in the art.

While topical administration is preferred, this compound may also be used in a intraocular implant as described in U.S. Published Patent Application 20050244463 which is hereby incorporated by reference. Such biocompatible intraocular implants include 4-bromo-N-imidazolidin-2-ylidene-1-H-benzimidazol-5-amine and a polymer associated with 4-bromo-N-imidazolidin-2-ylidene-1-H-benzimidazol-5-amine to facilitate release thereof into an eye for an extended period of time.

DETAILED DESCRIPTION OF THE INVENTION

Figure 1:
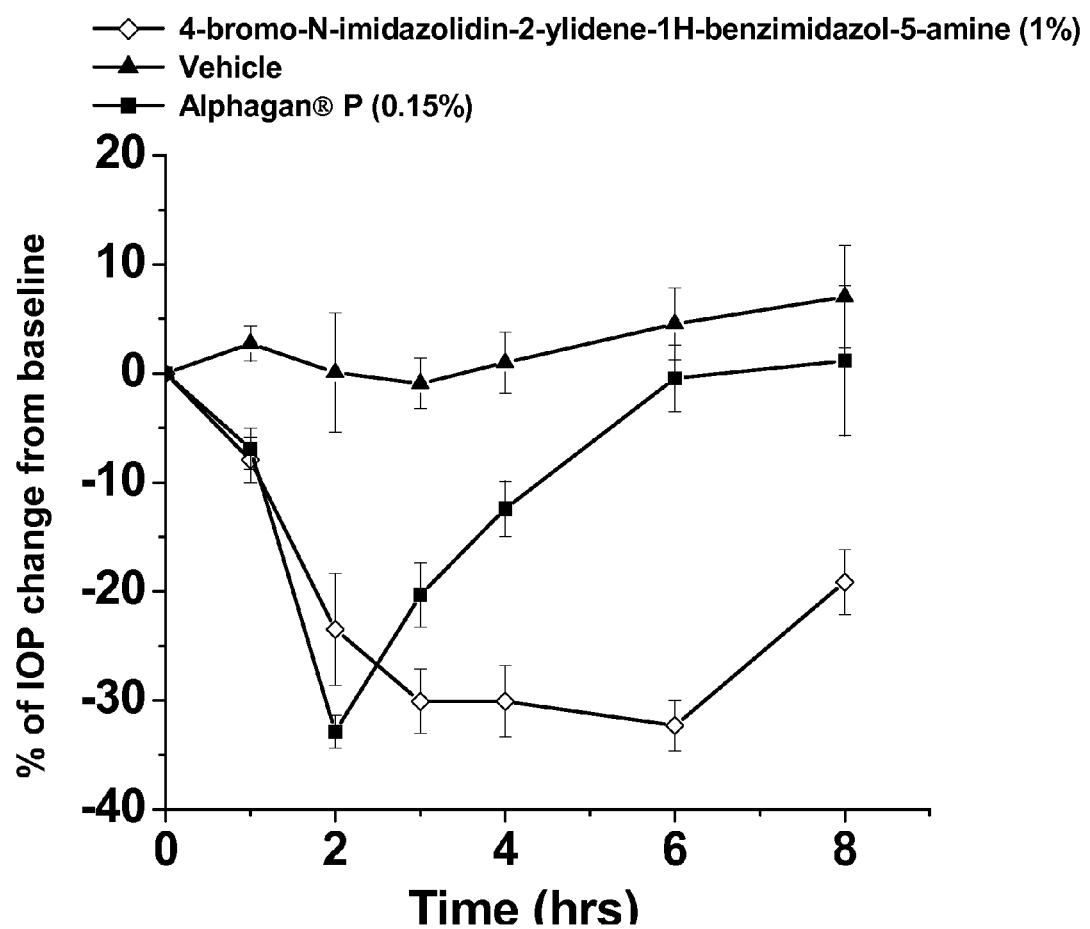
FIG. 1 shows that a 1% solution of 4-bromo-N-imidazolidin-2-ylidene-1-H-benzimidazol-5-amine lowers intraocular pressure in rabbits with unexpected long duration of action, i.e. over 8 hours, with no obvious side effects when compared to a 0.15% solution of brimonidine.

In one aspect of the invention, there is provided a method of lowering intraocular pressure of a patient in need thereof which comprises, consists essentially of or consists of administering a therapeutically effective amount of a pharmaceutical composition comprising, consisting essentially of or consisting of a therapeutically effective amount of 4-bromo-N-imidazolidin-2-ylidene-1-H-benzimidazol-5-amine or a salt thereof to the affected eye of said patient, as a single dose, wherein the affected eye maintains an intraocular pressure less than the baseline intraocular pressure for at least eight (8) hours and preferably at least ten (10) hours and more preferably at least twelve (12) hours, from the time of administration.

The term "baseline", as used herein, refers to the intraocular pressure measurement taken for the untreated eye.

In another aspect of the invention there is provided a method of treating a patient having elevated intraocular pressure with an alpha-2 adrenergic agonist to lower intraocular pressure, wherein the improvement comprises, consists essentially of or consists of lowering the elevated intraocular pressure for a prolonged period of at least eight (8) hours and preferably at least ten (10) hours and more preferably at least twelve (12) hours, by administering to the affected eye of said patient a single dose of a composition comprising, consisting essentially of or consisting of a therapeutically effective amount of 4-bromo-N-imidazolidin-2-ylidene-1-H-benzimidazol-5-amine.

In a still further aspect of the invention, there is provided a method of lowering intraocular pressure of a patient in need thereof which comprises administering a therapeutically effective amount of a composition comprising 4-bromo-N-imidazolidin-2-ylidene-1-H-benzimidazol-5-amine, to the affected eye of said patient, once or twice daily, preferably once daily, wherein the affected eye maintains an intraocular pressure less than the baseline intraocular pressure, throughout the day.

In one method of the invention, said intraocular pressure is lowered for at least eight (8) hours subsequent to administration.

In a preferred method of the invention, said intraocular pressure is lowered for at least ten (10) hours subsequent to administration.

In a more preferred method of the invention, said intraocular pressure is lowered for at least twelve (12) hours subsequent to administration.

In the method according to the present invention, the composition that is used, as a single dose, to lower intraocular pressure for at least eight (8) hours and preferably at least ten (10) hours and more preferably for at least twelve (12) hours, may comprise from 0.01 to 5 percent, preferably from 0.01 to 2 percent, more preferably from 0.05 to 2 percent by weight, 4-bromo-N-imidazolidin-2-ylidene-1-H-benzimidazol-5-amine in a pharmaceutically-acceptable vehicle. Said composition is preferably formulated as an eye drop suitable for topical administration.

In forming compositions for topical administration, the pharmaceutical compositions are preferably formulated as a solution in water at a pH of 5.5 to 8.0, e.g. about 6.9. While the precise regimen is left to the discretion of the clinician, it is recommended that the solution be topically applied by placing one drop in each eye one or two times, preferably once a day. Other ingredients which may be desirable to use in the ophthalmic preparations used in the method of the present invention include preservatives, co-solvents and viscosity building agents; sodium chloride, potassium chloride, calcium chloride dihydrate, magnesium chloride hexahydrate, boric acid and sodium borate decahydrate (as buffering agents) and purified water (*Clinical Ocular Pharmacology* By Jimmy D. Bartlett, Siret D. Jaanus, 2008, p 266).

Preservatives are thus required to prevent microbial contamination during use. Suitable preservatives include: stabilized oxychloro complex (sold under the trademark Purite™), stabilized chlorine dioxide, benzalkonium chloride, thimerosal, chlorobutanol, methyl paraben, propyl paraben, phenylethyl alcohol, edetate disodium, sorbic acid, Onamer M, or other agents known to those skilled in the art (*Review of Ophthalmology*, June 2001, Robert Noecker, MD). A common side-effect of these preservatives is burning. The method of the present invention offers the improvement of exposing the patient to less preservative, since the 4-bromo-N-imidazolidin-2-ylidene-1-H-benzimidazol-5-amine containing compositions are administered only once or at most, twice a day, unlike the prior art alpha-2 adrenergic agonists which require three doses, daily, to control elevated intraocular pressure. Typically, for the compositions utilized in the method of the present invention, the effective concentration of the preservative will range from 0.001% to 1%, preferably from 0.01% to 0.5%, by weight. In particular stabilized oxychloro complex (Purite®) will range from 0.001 to 0.01%, by weight.

The solubility of the components of the present compositions may be enhanced by a surfactant or other appropriate co-solvent in the composition. Such cosolvents include polysorbate 20, 60, and 80, Pluronic® F-68, F-84 and P-103, cyclodextrin, Solutol, or other agents known to those skilled in the art. Typically such co-solvents are employed at a level of from 0.01% to 2% by weight.

Viscosity increased above that of simple aqueous solutions may be desirable to increase ocular absorption of the active compound, to decrease variability in dispensing the formulation, to decrease physical separation of components of a suspension or emulsion of the formulation and/or to otherwise improve the ophthalmic formulation. Such viscosity building agents include as examples polyvinyl alcohol, polyvinyl pyrrolidone, methyl cellulose, hydroxypropyl methylcellulose, hydroxyethyl cellulose, carboxymethyl cellulose, hydroxypropyl cellulose or other agents known to those skilled in the art Such agents are typically employed at a level of from 0.01% to 2% by weight.

The following formulations are representative ophthalmic compositions of the invention for topical use when indicated for treating elevated intraocular pressure associated with glaucoma. In one example, the free base of 4-bromo-N-imidazolidin-2-ylidene-1-H-benzimidazol-5-amine was dissolved in sterile distilled water, hydrochloric acid was added and the hydrochloric salt of the compound was formed in situ. The solution was titrated with sodium hydroxide until the pH of the solution reached 8.0. The final concentration of 4-bromo-N-imidazolidin-2-ylidene-1-H-benzimidazol-5-amine is 1% by weight. In another example, the free base of 4-bromo-N-imidazolidin-2-ylidene-1-H-benzimidazol-5-amine was dissolved in sterile distilled water with boric acid, benzalkonium chloride and glycerin.

The present invention is not to be limited in scope by the exemplified embodiments, which are only intended as illustrations of specific aspects of the invention. Various modifications of the invention, in addition to those disclosed herein, will be apparent to those skilled in the art by a careful reading of the specification, including the claims, as originally filed. It is intended that all such modifications will fall within the scope of the appended claims.

EXAMPLE 1

This example shows the intraocular pressure lowering effect of 4-bromo-N-imidazolidin-2-ylidene-1-H-benzimidazol-5-amine containing composition, as compared to a composition comprising brimonidine. The free base of 4-bromo-N-imidazolidin-2-ylidene-1-H-benzimidazol-5-amine was dissolved in sterile distilled water, hydrochloric acid was added and the hydrochloric salt of the compound was formed in situ. The solution was titrated with sodium hydroxide until the pH of the solution reached 8.0. The final concentration of 4-bromo-N-imidazolidin-2-ylidene-1-H-benzimidazol-5-amine is 1% by weight. The experimental animals used were normotensive Dutch-Belted male rabbits. A single drop (50 µl) of the drug formulation was administered topically by pipette onto the right eye (treated eye) at approximately 07:00 AM hours. The intraocular pressure of the rabbits (treated and untreated eyes) was measured 0 hours before and at 0.5, 1, 2, 3, 4, 6 and 8 hours after topical eye drop single administration. The intraocular pressure taken before the eye drop administration (0 hours) was used as a baseline value. Prior to the tonometric measurements, 0.05% proparacaine (50 µl) was administered to each eye. Tonometric intraocular pressure measurements were obtained with a Mentor Pneumotonometer. Additionally, all studies were masked. All animals were examined for sedation, ocular irritation, and changes in pupil diameter throughout the course of the experiments. None of these effects were observed with high dose of compound. Therefore, the lack of systemic effects is confirmed. Pharmacokinetic studies have shown that the plasma level of 4-bromo-N-imidazolidin-2-ylidene-1-H-benzimidazol-5-amine is low confirming the low systemic exposure of this compound.

The results are reported in FIG. 1. As shown in FIG. 1, the intraocular pressure of the rabbits treated with the 4-bromo-N-imidazolidin-2-ylidene-1-H-benzimidazol-5-amine containing composition maintain the decrease in intraocular pressure for more than eight (8) hours, while the intraocular pressure of the rabbits treated with the brimonidine containing composition returns to baseline in less than six (6) hours.

EXAMPLE 2

This example shows the intraocular pressure lowering effect of 4-bromo-N-imidazolidin-2-ylidene-1-H-benzimidazol-5-amine containing composition, as compared to a composition comprising brimonidine. The free base of 4-bromo-N-imidazolidin-2-ylidene-1-H-benzimidazol-5-amine was dissolved in sterile distilled water, hydrochloric acid was added and the hydrochloric salt of the compound was formed in situ. The solution was titrated with sodium hydroxide until the pH of the solution reached 8.0. The final concentration of 4-bromo-N-imidazolidin-2-ylidene-1-H-benzimidazol-5-amine is 0.2% by weight. The experimental animals used were normotensive Dutch-Belted male rabbits. A single drop (50 µl) of the drug formulation was administered topically by pipette onto the right eye (treated eye) at approximately 07:00 AM hours. The intraocular pressure of the rabbits (treated and untreated eyes) was measured 0 hours before and at 2, 4 and 6 hours after topical eye drop single administration. The intraocular pressure taken before the eye drop administration (0 hours) was used as a baseline value. Prior to the tonometric measurements, 0.05% proparacaine (50 µl) was administered to each eye. Tonometric intraocular pressure measurements were obtained with a Mentor Pneumotonmeter. Additionally, all studies were masked. All animals were examined for sedation, ocular irritation, and changes in pupil diameter throughout the course of the experiments. None of these effects were observed with high dose of compound. Therefore, the lack of systemic effects is confirmed.

Figure 2:
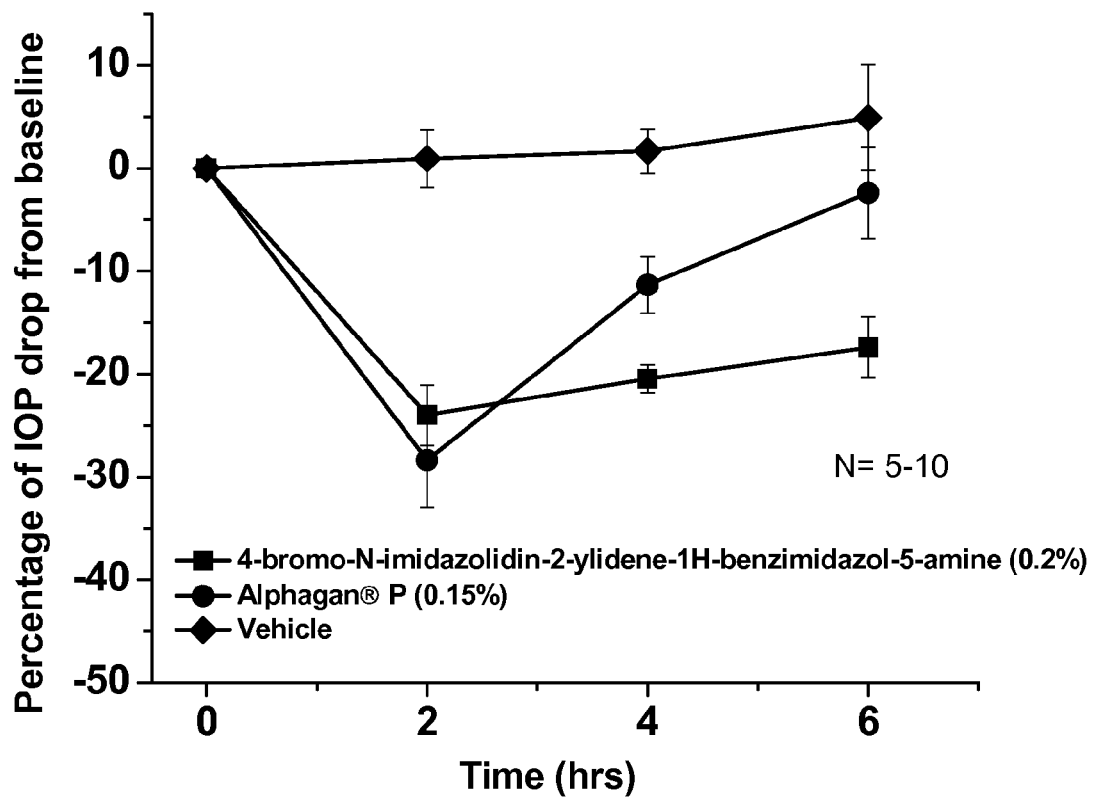
FIG. 2 shows that a 0.2% solution of 4-bromo-N-imidazolidin-2-ylidene-1-H-benzimidazol-5-amine lowers intraocular pressure in rabbits with unexpected long duration of action, i.e. over 6 hours, with no obvious side effects.

The results are reported in FIG. 2. As shown in FIG. 2, the intraocular pressure of the rabbits treated with the 4-bromo-N-imidazolidin-2-ylidene-1-H-benzimidazol-5-amine containing composition maintain the decrease in intraocular pressure for more than six (6) hours, while the intraocular pressure of the rabbits treated with the brimonidine containing composition returns to baseline in less than six (6) hours. The said compound in Example 1 and 2 clearly has a tendency to lower intraocular pressure (IOP) for extended period of time which is longer than that of ALPHAGAN® P

EXAMPLE 3

This example describes a pharmacokinetic analysis, which demonstrates that 4-bromo-N-imidazolidin-2-ylidene-1-H-benzimidazol-5-amine level in the aqueous humor is readily maintained for a prolonged period of time, unlike brimonidine.

Twenty-three Dutch Belted female rabbits (group 1) weighing approximately 1.75-2.34 kg were dosed with 35 µL of the formulation to the left eye. At different time points, prior to euthanasia, approximately 0.5 mL of blood was collected via central ear artery and placed in EDTA tubes. Blood samples were kept on ice during the duration of sample collection and centrifuged to harvest plasma. Animals were euthanized with 1 mL of Euthasol intravenously and the ocular tissues (aqueous humor, cornea, conjunctiva, iris-ciliary body, retina, and sclera) were collected from left and right eyes. All ocular tissues samples were placed in vials and kept on dry ice during the duration of sample collection. Ocular tissues were also collected from the control group (group 2) which received no dose. These ocular tissues served as analytical control. All ocular tissue and plasma samples were stored at or below −60° C. until bioanalysis. The analysis of the aqueous humor is reported in FIGS. 3 A/B. The results from this study are compared to results from a similar study done previously for 0.15% brimonidine. In addition, 4-bromo-N-imidazolidin-2-ylidene-1-H-benzimidazol-5-amine level is maintained for over 8 hrs in several ocular tissues whereas the plasma level was low and below detectable level.

Figures 3A, 3B:
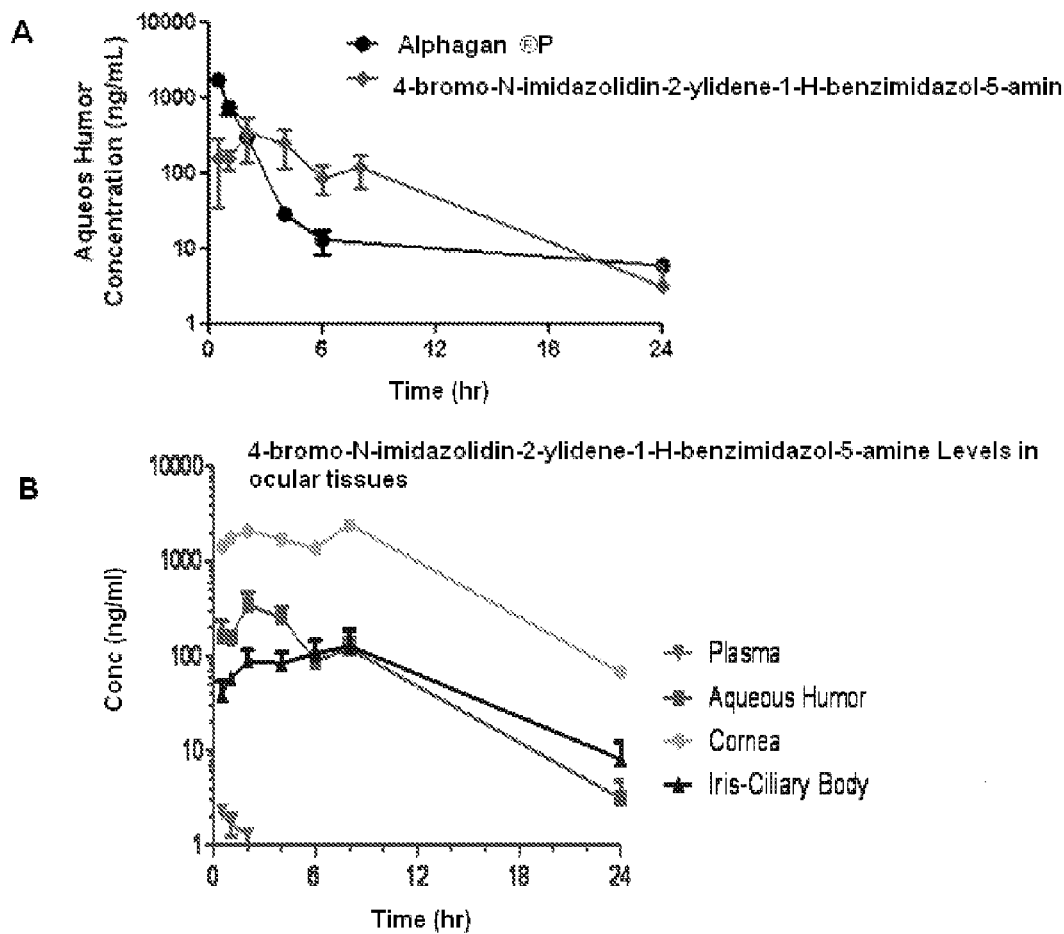
FIG. 3A shows the results of a pharmacokinetic analysis demonstrating that the concentration of 4-bromo-N-imidazolidin-2-ylidene-1-H-benzimidazol-5-amine in the aqueous humor is readily maintained for a prolonged period of time, unlike brimonidine.
FIG. 3B shows the results of a pharmacokinetic analysis demonstrating that the concentration of 4-bromo-N-imidazolidin-2-ylidene-1-H-benzimidazol-5-amine in the several ocular tissues is readily maintained for a prolonged period of time (>8 hrs).

The results are reported in FIG. 3 A which shows brimonidine levels in the aqueous humor are substantially decreased in 3 hours, while 4-bromo-N-imidazolidin-2-ylidene-1-H-benzimidazol-5-amine remains at sustained levels in the aqueous humor for over 8 hours. Published data showed that the level of brimonidine decreases in aqueous humor in three hours regardless of the dose. (Acheampong et al. (*Drug Metabolism and Disposition*, Vol 23, No. 7, p 708-712).

EXAMPLE 4

This example describes a corneal penetration assay which shows that 4-bromo-N-imidazolidin-2-ylidene-1-H-benzimidazol-5-amine penetrates the corneal epithelial cells poorly whereas brimonidine is a moderate penetrator. These results are reported in Table 1, below.

TABLE 1

| Compound | Papp ($\times 10^{-6}$ cm/s) |
|---|---|
| 3H-mannitol (test compound) | 0.512 ± 0.069 |
| Brimonidine | 8.57 ± 0.64 |
| 4-bromo-N-imidazolidin-2-ylidene-1-H-benzimidazol-5-amine | 0.119 ± 0.010 |

Papp=Permeability Coefficient

Based on permeability, the compound of the present invention is expected to have a shorter duration due to poor corneal penetration. However, unexpectedly this compound showed the opposite by decreasing the intraocular pressure for an extended period of time. This particular finding showed its unique feature compared to brimonidine. Compound 4-bromo-N-imidazolidin-2-ylidene-1-H-benzimidazol-5-amine has distinctive properties which allow it to control the intraocular pressure for an extended period of time in rabbits and monkeys; more importantly, the said compound in the invention has distinctive properties that allow it to control intraocular pressure (IOP) in human.

EXAMPLE 5

Figure 4:
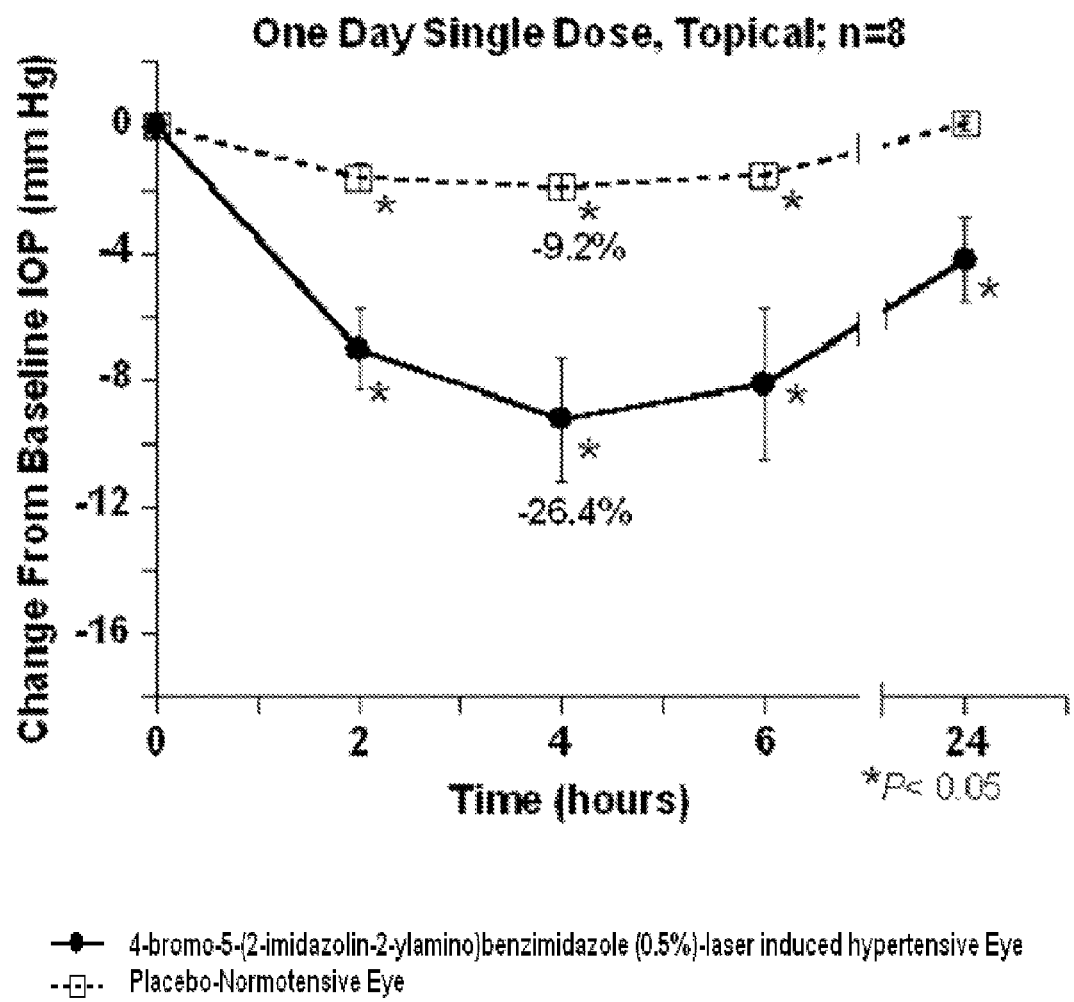
FIG. 4 shows that a 0.5% solution of 4-bromo-N-imidazolidin-2-ylidene-1-H-benzimidazol-5-amine lowers intraocular pressure in monkeys, with unexpected long duration of action, i.e. up to 24 hours, when compared to placebo.

This example shows the intraocular pressure -lowering effect of 4-bromo-N-imidazolidin-2-ylidene-1-H-benzimidazol-5-amine containing composition of Example 1 as compared to placebo. The results are reported in FIG. 4. As shown in FIG. 4, the intraocular pressure of the monkeys treated with the 4-bromo-N-imidazolidin-2-ylidene-1-H-benzimidazol-5-amine containing composition, maintain the decrease in intraocular pressure for up to 24 hours.

What is claimed:
1. A method of lowering intraocular pressure, the method comprising administering a therapeutically effective amount of a pharmaceutical composition comprising 4-bromo-5-(2-imidazolin-2-ylamino)benzimidazole or a salt thereof, by direct injection to an affected eye of a patient once or twice per day, such that the affected eye has an intraocular pressure less than the baseline intraocular pressure for at least six (6) hours.

2. The method of claim 1, wherein the affected eye maintains an intraocular pressure less than the baseline intraocular pressure for at least eight (8) hours.

3. The method of claim 1, wherein the affected eye maintains an intraocular pressure less than the baseline intraocular pressure for at least ten (10) hours.

4. The method of claim 1, wherein the composition comprises 0.01% to 5% by weight, 4-bromo-5-(2-imidazolin-2-ylamino)benzimidazole or a salt thereof.

5. The method of claim 1, wherein the composition comprises 0.15% to 1% by weight, 4-bromo-5-(2-imidazolin-2-ylamino)benzimidazole or a salt thereof.

6. The method of claim 1, wherein the composition further comprises from 0.001% to 1% by weight of a preservative.

7. The method of claim 1, wherein the composition further comprises from 0.01% to 0.5% by weight of a preservative.

8. The method of claim 1, wherein the composition further comprises from 0.001% to 0.01% by weight of a preservative.

9. The method of claim 1, wherein the composition further comprises from 0.01% to 1% by weight of a co-solvent.

10. The method of claim 1, wherein the composition further comprises from 0.01% to 2% by weight of a viscosity building agent.

11. The method of claim 1 wherein 4-bromo-5-(2-imidazolin-2-ylamino)benzimidazole is undetectable in the systemic circulation subsequent to administration.

12. The method of claim 1, wherein 4-bromo-5-(2-imidazolin-2-ylamino)benzimidazole is maintained in the aqueous humor for at least ten (10) hours.

13. The method of claim 1, wherein said composition is administered once a day.

\* \* \* \* \*